(12) United States Patent
Schmitt et al.

(10) Patent No.: US 9,145,362 B2
(45) Date of Patent: *Sep. 29, 2015

(54) SOLVENT COMPOSITION BASED ON AN OXIDE OF AN ORGANIC SULFIDE WITH MASKED ODOUR

(75) Inventors: Paul-Guillaume Schmitt, Lescar (FR); Bernard Monguillon, Mourenx (FR); Mélanie Vauthrin, Denguin (FR)

(73) Assignee: ARKEMA FRANCE, Colombes Cedex (FR)

( * ) Notice: Subject to any disclaimer, the term of this patent is extended or adjusted under 35 U.S.C. 154(b) by 664 days.

This patent is subject to a terminal disclaimer.

(21) Appl. No.: 13/381,718

(22) PCT Filed: Jul. 29, 2010

(86) PCT No.: PCT/FR2010/051615
§ 371 (c)(1),
(2), (4) Date: Jan. 26, 2012

(87) PCT Pub. No.: WO2011/012820
PCT Pub. Date: Feb. 3, 2011

(65) Prior Publication Data
US 2012/0132858 A1 May 31, 2012

Related U.S. Application Data

(60) Provisional application No. 61/234,680, filed on Aug. 18, 2009.

(30) Foreign Application Priority Data

Jul. 31, 2009 (FR) ..................... 09 55398
Jan. 12, 2010 (FR) ..................... 10 50157

(51) Int. Cl.
| | | |
|---|---|---|
| C07C 317/02 | (2006.01) | |
| C07C 315/06 | (2006.01) | |
| C07C 317/00 | (2006.01) | |
| C07C 319/26 | (2006.01) | |

(52) U.S. Cl.
CPC ............ *C07C 315/06* (2013.01); *C07C 317/00* (2013.01); *C07C 317/02* (2013.01); *C07C 319/26* (2013.01)

(58) Field of Classification Search
CPC ........................... C07C 317/00; C07C 317/02
USPC .................. 568/18, 19, 21, 27; 252/384, 364
See application file for complete search history.

(56) References Cited

U.S. PATENT DOCUMENTS

| 4,145,391 A * | 3/1979 | Rodier ........................... 264/83 |
| 6,042,640 A | 3/2000 | Isganitis |
| 2001/0005766 A1 | 6/2001 | Fremy |
| 2009/0005601 A1 | 1/2009 | Kvakovszky |

FOREIGN PATENT DOCUMENTS

EP 0976726 A1 2/2000

OTHER PUBLICATIONS

International Search Report received in PCT/FR2010/051615, mailed Dec. 2, 2010.

* cited by examiner

*Primary Examiner* — Khanh Tuan Nguyen
*Assistant Examiner* — Haidung Nguyen
(74) *Attorney, Agent, or Firm* — Smith, Gambrell & Russell, LLP

(57) ABSTRACT

The invention relates to solvent compositions predominantly comprising at least one oxide of an organic sulfide, more particularly dimethyl sulfoxide, to which is added at least one odour-masking agent comprising at least one compound selected from monoesters, diesters or triesters, alcohols, ketones, aldehydes and terpenes.

29 Claims, No Drawings

SOLVENT COMPOSITION BASED ON AN OXIDE OF AN ORGANIC SULFIDE WITH MASKED ODOUR

This application is a 371 National Phase application of PCT/FR2010/051615 which claims the benefit of U.S. Patent Application Serial No. 61/234,680, filed 18 Aug. 2009, and FR 0955398, filed 31 Jul. 2009, and FR 1050157, filed 12 Jan. 2010, which are herein incorporated by reference in their entirety.

The present invention relates to the field of organic sulfides and more particularly to that of oxides of alkyl or dialkyl sulfides, and especially dimethyl sulfoxide (or DMSO).

It is well known that organic sulfides generally have a strong, unpleasant or even aggressive odor. The oxides of organic sulfides, in particular DMSO, may have a less aggressive odor, but, however, depending on the concentrations of impurities, this odor may be unpleasant and a nuisance to the final user.

Hitherto, this drawback has not constituted a real problem since the oxides of organic sulfides, and in particular DMSO, are generally used in small amounts, usually in compositions, for example pharmaceutical, cosmetic, plant-protection and similar compositions. Such compositions comprise many other components, which are very often much more odorous, or even malodorous, the odors of which are commonly masked with solvents, aromas, fragrances and the like. Thus, the drawbacks associated with the odor of the oxides of organic sulfides have hitherto not constituted a real problem with which a person skilled in the art has been confronted.

However, the oxides of organic sulfides, and in particular DMSO, are nowadays liable to find other uses in which their odors might represent an impediment to their development. Specifically, on account of the scheduled replacement of toxic solvents, for instance N-methylpyrrolidone (NMP), N,N-dimethylformamide (DMF) or methylene chloride, oxides of organic sulfides, and in particular DMSO, represent solvents of choice on account of their properties, namely their low toxicity and their high solvent power.

For the use of oxides of organic sulfides as solvents, the problem of the inherent odors of these products thus remains to be solved. The Applicant has now discovered that it is possible to mask or odorize oxides of organic sulfides used as solvents in order to enable their uses without being inconvenienced by the intrinsic odors of said oxides, while at the same time conserving the solvent properties intrinsic to said oxides of organic sulfides.

Thus, one subject of the invention is a solvent composition comprising:
a) at least 50% and preferably at least 70%, and most preferably at least 80% by weight of at least one oxide of an organic sulfide of general formula (1):

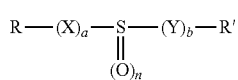 (1)

in which
 X and Y, which may be identical or different, are chosen, independently of each other, from oxygen, sulfur, —SO—, —SO$_2$—, —NH— and —NR"—;
 a and b, which may be identical or different, represent, independently of each other, 0 or 1; n is equal to 1 or 2;
 R, R' and R", which may be identical or different, are chosen, independently of each other, from a linear or branched alkyl radical containing from 1 to 12 carbon atoms, a linear or branched alkenyl radical containing from 2 to 12 carbon atoms, and an aryl radical containing from 6 to 10 carbon atoms; R, R' and R" possibly being substituted with radicals chosen from alkyl, alkenyl, aryl and halogen, and possibly containing one or more heteroatoms chosen from O, S, N, P and Si; R and R' also possibly forming, together with the atoms that bear them, a hydrocarbon-based cyclic structure optionally containing one or more heteroatoms chosen from O, S and N, said cyclic structure comprising in total 5, 6, 7, 8 or 9 ring members; and
b) from a few ppm, advantageously 10 ppm, to 2%, preferably from 10 ppm to 1%, by weight relative to the total weight of the composition, of at least one odor-masking agent comprising at least one compound chosen from monoesters, diesters and/or triesters, alcohols, aldehydes, ketones and terpenes.

The amount of masking agent (composition b)) may vary within wide proportions in the range indicated above, depending on the desired effect, the intensity of the odor to be masked, the respective residual contents of the various impurities that may be present in the component(s) a) defined previously, and the like.

Amounts of masking agent of less than a few ppm may be too low to obtain the desired effect. Amounts of masking agent greater than 2% may have harmful effects depending on the intended applications for the oxides of organic sulfides as solvents.

Preferably, and in a nonlimiting manner, the content of odor-masking agent(s) b) is between 0.001% and 0.2% by weight relative to the total weight of the composition and preferably between 100 ppm and 1000 ppm, for example about 500 ppm by weight.

In the description of the present invention, the percentages are indicated on a weight basis, unless specifically mentioned otherwise. Unless otherwise mentioned, "ppm" means parts per million by weight. The term "aryl radical" means an aromatic hydrocarbon-based radical preferably chosen from phenyl and naphthyl. Preferably, the aryl radical is a phenyl radical.

According to one preferred aspect of the present invention, component a) corresponds to formula (1) in which a is 0 and —(Y)$_b$— represents —(S)$_x$—, in which x represents 0 or 1, preferably 0. Preference is also given to the components a) of formula (1) for which the radicals R and R' are identical and chosen, independently of each other, from a linear or branched alkyl radical comprising from 1 to 12 carbon atoms, preferably from 1 to 6 carbon atoms and more preferably from 1 to 4 carbon atoms, a linear or branched alkenyl radical comprising from 2 to 12 carbon atoms, preferably from 2 to 6 carbon atoms and more preferably from 2 to 4 carbon atoms, and an aryl radical, preferably phenyl.

According to another preferred aspect, among the components a) of formula (1) above, those for which a and b each represent 1 and X and Y are chosen independently from oxygen, sulfur, —NH— and —NR"— are preferred.

According to one embodiment, component a) used in the composition according to the present invention is an oxide of an organic sulfide, obtained according to any process that is known per se, or alternatively commercially available, and preferably having a reduced content of volatile impurities. Such impurities are, for example, and especially when compound a) is DMSO, dimethyl sulfide (DMS), dimethyl disulfide (DMDS) and/or bis(methylthio)methane, also known as 2,4-dithiapentane (BMTM).

Any method known to those skilled in the art for removing, or at the very least reducing, the abovementioned volatile impurities may be suitable for use, among which mention may be made, in a nonlimiting manner, of distillation, crystallization, evaporation under a stream of inert gas such as nitrogen, air, and the like.

In the case of DMSO, the contents of impurities, such as DMS, DMDS and/or BMTM, should advantageously be less than 100 ppm, preferably less than 50 ppm and more preferably less than 10 ppm, for each of the impurities taken separately.

According to one preferred embodiment, component (a) of the composition according to the present invention corresponds to formula (1'):

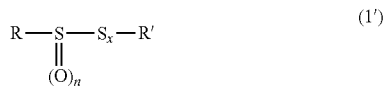

in which R is chosen from a linear or branched alkyl radical containing from 1 to 4 carbon atoms, a linear or branched alkenyl radical containing from 2 to 4 carbon atoms, and an aryl radical, preferably phenyl, n is equal to 1 or 2; x represents 0 or 1; R' is chosen from a linear or branched alkyl radical containing from 1 to 4 carbon atoms, a linear or branched alkenylene radical containing from 2 to 4 carbon atoms, and an aryl radical, preferably phenyl.

According to one particularly preferred embodiment, component a) of the composition according to the present invention corresponds to formula (1a):

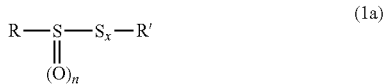

in which R and R', which may be identical or different, are chosen from a linear or branched alkyl radical containing from 1 to 4 carbon atoms, a linear or branched alkenyl radical, containing from 1 to 4 carbon atoms, and a phenyl radical; n is equal to 1 or 2; and x is equal to 0.

Preferably, component a of formula (1a) is DMSO.

According to the invention, the masking of the odor of the oxide of an organic sulfide corresponding to formula (1), (1') or (1a) described previously is obtained by adding to said oxide a composition defined in b) previously.

The present invention has the advantage of masking the unpleasant odor of at least one oxide of an organic sulfide, without chemically modifying its nature. Thus, the present invention proposes a composition comprising a) a major amount of at least one oxide of an organic sulfide of formula (1), (1') or (1a) defined previously, to which is added a minor amount of a composition b) that masks the unpleasant odor of component a).

The composition with masked odor according to the present invention may be prepared according to any process that is known per se by simply combining at least one component a) with at least one odor-masking composition b). It is possible, for example, to add at least one composition b) to at least one component a), or vice versa, optionally with stirring and/or optionally with heating. More generally, any known mixing and/or heating method may be used.

The preparation of the composition according to the invention may be performed, for example, at atmospheric pressure, at a temperature of between 0° C. and 100° C., and preferably between room temperature and about 80° C. The preparation may also be performed under a positive pressure or under a negative pressure, at temperatures within the ranges indicated above.

The time period required for the preparation of the composition with masked odor according to the invention varies according to the nature and amount of the component(s) a) and of the composition(s) b), but also as a function of the chosen temperature and pressure. As a general rule, this time corresponds to the time necessary to obtain a homogeneous mixture that produces the desired effect of masking the odor of the component(s) a); it is generally between a few seconds and a few minutes, or even one or more hours.

The preparation process mentioned above may be performed in batch mode (batch process) or in continuous mode.

As indicated previously, the odor-masking agent b) comprises one or more compounds chosen from:
 b1) monoesters;
 b2) diesters and/or triesters;
 b3) alcohols, advantageously monoalcohols, comprising from 1 to 30 carbon atoms, preferably from 6 to 20 carbon atoms and more preferably from 8 to 11 carbon atoms, said carbon atoms forming a linear or branched chain optionally comprising one or more unsaturation(s) in the form of double bonds, and optionally comprising a 5- or 6-membered cyclic structure, which is saturated or partially or totally unsaturated;
 b4) aldehydes and/or ketones, in particular aldehydes and/or ketones of formula $R^a$—CO—$R^b$, in which $R^a$ represents a linear or branched hydrocarbon-based chain comprising from 1 to 6 carbon atoms, optionally comprising one or more unsaturation(s) in the form of double bonds, and $R^b$ represents a hydrogen atom, a cyclic hydrocarbon-based chain or a linear or branched hydrocarbon-based chain, optionally, but preferably, substituted with a cyclic structure, $R^b$ comprising from 6 to 12 carbon atoms, optionally comprising one or more unsaturation(s) in the form of double bonds and being optionally substituted with one or more hydroxyl groups; and
 b5) terpenes.

As illustrative but nonlimiting examples of monoesters mentioned in b1), mention may be made of esters of saturated or unsaturated $C_2$-$C_{20}$ acids, such as acetates, propionates, butyrates, methylbutyrates, pentanoates, hexanoates, heptanoates, caproates, oleates, linoleates or linolenates of ethyl, propyl, butyl, pentyl, 2-methylbutyl, isoamyl, hexyl, benzyl, phenylethyl, menthyl, carvyl, and the like, and also mixtures thereof.

Isoamyl acetate, hexyl acetate, 2-methylbutyl butyrate, isoamyl butyrate, benzyl acetate and phenylethyl acetate, and mixtures of these compounds, are more particularly preferred.

As illustrative but nonlimiting examples of diesters and/or triesters b2), mention may be made of ortho-phthalates, such as diethyl ortho-phthalate; citrates, such as triethyl citrate; and/or malonates, such as diethyl malonate.

As illustrative but non-limiting examples of alcohols b3) mentioned previously, mention may be made preferably of monoalcohols, the hydroxyl function of which is preferably borne by an $sp^2$ carbon atom. It should be understood that the hydroxyl function may also be borne by a carbon atom included in a cyclic structure as defined previously.

The alcohols b3) that may be used in the odor-masking agent and as defined above are advantageously, and as nonlimiting examples, chosen from menthol, neomenthol, phenylethyl alcohol, benzyl alcohol, citronellol, dihydromyrcenol, dihydroterpineol, dimetol, ethyllinalool, geraniol, linalool, tetrahydrolinalool, tetrahydromyrcenol, nerol, and the like, and also mixtures of two or more thereof.

As illustrative but nonlimiting examples of aldehydes and ketones mentioned in b4), mention may preferably be made of propionaldehyde, butyraldehyde, valeraldehyde, capraldehyde, benzaldehyde, geranial, neral, citronellal and, in general, aldehydes containing hydrocarbon-based groups comprising one or more unsaturations of olefinic type, menthone, isomenthone, 1,8-cineole, ascaridole, flavonone, damascones, damascenones, ionones, irisones, methyl-ionones, frambinone (CAS No. 5471-51-2), and the like, and also mixtures of two or more thereof in all proportions.

As illustrative but nonlimiting examples of terpenes indicated in b5), examples that may be mentioned include terpinenes, myrcene, limonene, terpinolene, pinenes, sabinene, camphene, and the like, mixtures of two or more thereof, and also terpene-based essences, especially those comprising these ingredients.

In addition, the odor-masking agent b) that may be used in the context of the present invention may comprise, in minor amounts, other agents (fragrances) usually used in the field of perfumery.

Composition b) for masking the odor of organic sulfides, and as described previously, may, where appropriate, or if necessary, also comprise one or more additives commonly used in the field. Such additives may be chosen, for example, and in a nonlimiting manner, from solvents, pigments, dyes, preserving agents, biocides, and the like.

Among the solvents, examples that are most particularly preferred are alcohols, ethers, esters and glycols. In a particularly advantageous manner, the solvent is chosen from diethyl phthalate, ethylene glycol, propylene glycol, diethylene glycol, dipropylene glycol, polyethylene glycols, polypropylene glycols, and mixtures thereof, and even more advantageously from diethyl phthalate, dipropylene glycol, and mixtures thereof.

It should be understood that the monoesters, diesters or triesters present in the composition of odor-masking agent b), as component b1) and/or b2), may also have the functions of the solvents defined above.

According to one preferred aspect, the odor-masking agent used in the composition of the present invention is chosen from odor-masking agents comprising:
at least one component b1);
at least one component b1) and at least one component b2);
at least one component b1) and at least one component b3);
at least one component b1) and at least one component b4);
at least one component b1) and at least one component b5);
at least one component b1), at least one component b2) and at least one component b3);
at least one component b1), at least one component b2) and at least one component b4);
at least one component b1), at least one component b2) and at least one component b5);
at least one component b1), at least one component b3) and at least one component b4);
at least one component b1), at least one component b3) and at least one component b5);
at least one component b1), at least one component b2), at least one component b3) and at least one component b4);
at least one component b1), at least one component b2), at least one component b3) and at least one component b5);
at least one component b1), at least one component b2), at least one component b3), at least one component b4) and at least one component b5);
at least one component b2);
at least one component b2) and at least one component b3);
at least one component b2) and at least one component b4);
at least one component b2) and at least one component b5);
at least one component b2), at least one component b3) and at least one component b4);
at least one component b2), at least one component b3) and at least one component b5);
at least one component b2), at least one component b4) and at least one component b5);
at least one component b2), at least one component b3), at least one component b4) and at least one component b5);
at least one component b3);
at least one component b3) and at least one component b4);
at least one component b3) and at least one component b5);
at least one component b3), at least one component b4) and at least one component b5);
at least one component b4);
at least one component b4) and at least one component b5); and
at least one component b5).

According to an even more preferred aspect, the odor-masking agent used in the composition of the present invention is chosen from odor-masking agents comprising:
at least one component b1), at least one component b2) and at least one component b3);
at least one component b1), at least one component b2) and at least one component b4);
at least one component b1), at least one component b2) and at least one component b5);
at least one component b1), at least one component b2), at least one component b3) and at least one component b4);
at least one component b1), at least one component b2), at least one component b3) and at least one component b5); and
at least one component b1), at least one component b2), at least one component b3), at least one component b4) and at least one component b5).

As indicated previously, the composition according to the present invention comprises at least one composition of odor-masking agent b), said agent comprising from 1% to 40%, preferably from 2% to 35% and more preferably from 5% to 30% by weight, relative to the total weight of composition b), of at least one monoester mentioned in b1).

The composition of odor-masking agent b) also comprises at least one diester and/or triester b2), in an amount ranging from 10% to 70% by weight, preferably from 15% to 65% by weight and more preferably from 20% to 60% by weight relative to the total weight of composition b).

The odor-masking agent b) also comprises from 1% to 30% and preferably from 5% to 25% by weight, relative to the total weight of the composition, of at least one alcohol b3).

The amount of aldehyde(s) or of ketone(s) indicated in b4) is advantageously within a proportion ranging from 0.5% to 20% and preferably from 1% to 10% by weight relative to the total weight of the composition.

The odor-masking agent may optionally also comprise up to 20% and preferably from 1% to 10% by weight, relative to the total weight of the composition, of at least one terpene indicated in b5).

According to one preferred embodiment, the odor-masking agent b) comprises:
b1) from 1% to 40% by weight of at least one monoester;
b2) from 10% to 70% by weight of at least one diester and/or triester;
b3) from 1% to 30% of at least one alcohol;
b4) from 0.5% to 20% of at least one aldehyde or ketone of formula $R^a$—CO—$R^b$, in which $R^a$ represents a linear or branched hydrocarbon-based chain comprising from 1 to 6 carbon atoms, optionally comprising one or more unsaturation(s) in the form of double bonds, and $R^b$ represents a hydrogen atom, a cyclic hydrocarbon-based chain or a linear or branched hydrocarbon-based chain, optionally, but preferably, substituted with a cyclic structure, $R^b$ comprising from 6 to 12 carbon atoms, optionally comprising one or more unsaturation(s) in the form of double bonds and being optionally substituted with one or more hydroxyl groups; and b5) optionally up to 20% of at least one terpene.

A typical composition of odor-masking agent that is suitable for the oxides of organic sulfides according to the present invention comprises, on a weight basis:

from 5% to 30% by weight of at least one monoester b1), chosen from isoamyl acetate, ethyl 2-methyl-butyrate, isoamyl butyrate, phenylethyl acetate, ethyl caproate, -benzyl acetate and hexyl acetate, and mixtures thereof;

from 20% to 60% by weight of at least one diester and/or triester b2) chosen from ortho-phthalates, such as diethyl ortho-phthalate; citrates, such as triethyl citrate; malonates, such as diethyl malonate, and mixtures thereof;

from 5% to 25% of at least one alcohol, preferably of at least two alcohols, and more preferably of at least three alcohols, as described previously in b3);

from 1% to 10% of at, least one ketone, preferably at least two ketones, more preferably at least three ketones, as described previously in b4); and from 1% to 10% of at least one, preferably at least two, and preferably a mixture of terpenes referenced above in b5).

This composition, noted $C_i$ in the rest of the present specification, is most particularly suitable for masking the odor and improving the odor of oxides of organic sulfides, and in particular of DMSO.

A representative but nonlimiting example of such a composition $C_i$ is reproduced below, in which each of the components comprises one, several or even all the listed compounds:

| Component b1) | |
|---|---|
| comprising benzyl acetate, hexyl acetate, isoamyl acetate, phenylethyl acetate, ethyl caproate, ethyl 2-methylbutyrate | 16.00% |
| Component b3) | |
| comprising phenylethyl alcohol, citronellol, geraniol, linalool, cis-3-hexenol | 20.60% |
| Component b4) | |
| comprising 1-(4-hydroxyphenyl)-3-butanone, alpha-irisone | 4.50% |
| Component b5) | |
| orange terpenes | 7.00% |
| Others | |
| comprising citral, ethylmaltol, ethylmethyl-phenyl glycidate | 1.90% |
| Component b2) | |
| comprising diethyl malonate, diethyl phthalate qs | 100.00% |

These compositions of masking agents for the oxides of organic sulfides used as solvent are given as examples and are in no way limiting as regards the potential diversity of compositions permitted by the present invention defined with the aid of the attached claims.

According to another aspect, the present invention relates to a solvent composition comprising:

a) from 50% to 95%, preferably from 70% to 90% and most preferably about 80% by weight of at least one oxide of an organic sulfide of general formula (1) as defined previously;

b) from a few ppm, advantageously from 10 ppm, to 2%, preferably from 10 ppm to 1% by weight, relative to the total weight of the composition, of at least one odor-masking agent b) as defined previously; and c) from 5% to 50%, preferably from 10% to 30% and most preferably about 20% by weight of at least one cosolvent.

The cosolvent is typically chosen from compounds that are at least partially or totally soluble in the oxides of organic sulfides a), and in particular in DMSO.

Thus, the cosolvent is preferably chosen from carbonates, esters, ketones, amines, amides and alcohols, more preferably from alcohols, which are preferably saturated, preferably comprising from 1 to 10 carbon atoms, and chosen, for example and in a nonlimiting manner, from methanol, ethanol, propanol, butanol, pentanol, ethylene glycol, propylene glycol and glycerol (1,2,3-propanetriol), preferably from methanol, ethanol, ethylene glycol and glycerol. A preferred cosolvent is glycerol.

A composition that is most particularly preferred according to the present invention comprises:

a) from 50% to 95%, preferably from 70% to 90% and most preferably about 80% by weight of at least one oxide of an organic sulfide of general formula (1), (1') or (1a) as defined previously, and preferably DMSO;

b) from a few ppm, advantageously from 10 ppm, to 2%, preferably from 10 ppm to 1% by weight, relative to the total weight of the composition, of at least one odor-masking agent b) as defined previously, preferably the masking agent $C_i$; and c) from 5% to 50%, preferably from 10% to 30% and most preferably about 20% by weight of an alcohol, preferably glycerol.

For example, a composition according to the present invention comprises:

a) about 80% by weight of DMSO;

b) from a few ppm, advantageously from 10 ppm, to 2%, preferably from 10 ppm to 1% by weight, relative to the total weight of the composition, of masking agent $C_i$; and, c) about 20% by weight of glycerol.

The solvent compositions according to the present invention predominantly comprising at least one oxide of an organic sulfide and at least one odor-masking agent find most advantageous uses in numerous fields, where such solvents are used little or not at all, especially on account of their odor.

Such uses that are now possible are, for example, the use of solvent predominantly based on oxide(s) of organic sulphide(s), and in particular of DMSO, as cleaning or stripping solutions (for paints, in the electronics field, for photoresist stripping, and the like), agrochemical formulations, in particular pesticidal formulations (herbicides, insecticides, fungicides, bactericides, nematicides and the like), defrosting formulations, compositions for coolant fluids and other formulations for the synthesis or dissolution (cleaning or forming) of resins and/or polymers, among which mention may be made of polyacrylates, polymethacrylates, polyacrylonitrile, poly(vinyl acetate), polyimides (for instance polyesterimides, polyamideimides, polyetherimides and poly(aminobismaleimides), polysulfones, polyesters, poly(vinyl alcohols), polyether sulfones, polyamides, polyurethanes, elastomers (for instance EPDMs and SBRs), epoxy resins, phenoplast resins, aminoplast resins, chlorinated polymers (such as PVC), fluorinated polymers (such as PTFE and PVDF, in particular the various grades of Kynar® sold by the company Arkema, and especially Kynar Flex®), to mention but a few of the possible uses, without being limiting.

The examples that follow illustrate the invention without limiting it.

EXAMPLE 1

Masked-odor DMSO-based Composition

In order to characterize a fragrancing composition for masking or improving the odor of DMSO, an olfactory test procedure was developed. This procedure makes it possible to classify various formulations hedonically.

Operating Conditions:

To perform this olfactory test, 30-liter polyethylene (PE) drums are used, each fitted with a lid in which is cut a trapdoor of about 10 cm×10 cm, enabling an operator (panelist) to smell the vapors contained in the drum.

A crystallizing dish containing 2 sheets of blotting paper (chromatographic paper) is placed in each of the drums. 1 ml of test composition is poured onto each sheet. The drums are kept closed for 24 hours at room temperature. The evaluation is then performed under blind conditions.

The panelists, of whom there are 10, take turns to test a few products per session (a maximum of 3 products per session). They start by smelling the drum which contains the reference DMSO of this study, and then one of the test compositions.

The panelists attribute, according to their preference, a grade to each of the test compositions, relative to the reference which arbitrarily received the grade 5. The grades given by the panelists range from 1 (the most pleasant product) to 10 (the most unpleasant product).

Preparation of the Test Samples:

The reference DMSO is an industrial DMSO of purity equal to 99.97%, produced by Arkema, and then supplemented with 50 ppm of dimethyl sulfide (DMS). This sample is named $B_1$.

The same batch of DMSO supplemented with 50 ppm of dimethyl sulfide is supplemented with 700 ppm of the fragrancing composition C, according to the invention. This sample is named $B_2$.

The results of the olfactory test are given in table 1 below:

TABLE 1

| Test sample | Mean | Standard deviation | Group |
|---|---|---|---|
| $B_1$ | 5.93 | 1.33 | A |
| $B_2$ | 2.75 | 1.52 | B |

Statistical processing of these results makes it possible to calculate the standard deviation and to classify the samples into two groups by studying the SSD (smallest significant difference) given in this test at 1.01.

The SSD test is a statistical test of comparison of means and makes it possible to determine whether the means of two samples are significantly different or not, from a statistical point of view.

In the examples of the present invention, the statistical parametization used is set at 95%. If the means are not significantly different, the two samples are classified in the same group. If the means are significantly different, the two samples constitute two separate groups (A and B in the illustrative examples of the invention).

The same operation is performed to compare all the samples, which makes it possible at the end to arrive at 1, 2 or more groups, each consisting of samples whose mean grades are not significantly different. These various processing methods are performed using the software FIZZ version 2.01 (Biosystemes, Couternon, France).

There is thus a very significant statistical difference indicating a markedly more pleasant perception of the odor of sample $B_2$ than of sample $B_1$.

EXAMPLE 2

Masked-odor DMSO-based Composition

The same industrial DMSO as that of example 1, of purity 99.97%, produced by Arkema, is tested without addition of the 50 ppm of DMS, according to the olfactory test described in example 1. This sample is named $C_1$.

150 ppm of the fragrancing composition $C_i$ according to the invention are added to this same industrial DMSO. This sample is named $C_2$.

The results of the olfactory test on $C_1$ and $C_2$ indicate that the sample $C_2$ is judged to be statistically markedly more pleasant than the sample $C_1$.

EXAMPLE 3

Masked-odor DMSO-based Composition

The same industrial DMSO as that of example 1, of purity 99.97%, produced by Arkema, is tested without addition of the 50 ppm of DMS, according to the olfactory test described in example 1. This sample is named $C_1$.

50 ppm of the fragrancing composition $C_i$ according to the invention are added to this same industrial DMSO. This sample is named $D_2$.

50 ppm of a fragrancing composition consisting of 100% essence of pine (Societe D. R. T., Dax, France) which is a mixture of monoterpenes and of cineols: terpinolene, dipentene, 1,4-cineol and 1,8-cineol, are added to this same industrial DMSO $C_1$. This sample is named $D_3$.

The results of the olfactory test are given in table 2 below:

TABLE 2

| Test sample | Mean | Group |
|---|---|---|
| $C_1$ | 5 | A |
| $D_2$ | 3.68 | B |
| $D_3$ | 4 | B |

A fragrancing composition based on essence of pine thus makes it possible to render the odor of sample $C_1$ more pleasant, like the fragrancing composition $C_i$ according to the invention.

The invention claimed is:
1. A solvent composition comprising:
a) at least 50% by weight of at least one oxide of an organic sulfide of general formula (1):

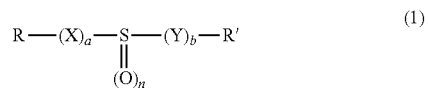

$$R\text{---}(X)_a\text{---}\underset{\underset{(O)_n}{\|}}{S}\text{---}(Y)_b\text{---}R' \tag{1}$$

in which
X and Y, which may be identical or different, are chosen, independently of each other, from oxygen, sulfur, —SO—, —SO$_2$—, —NH— and —NR"—;
a and b, which may be identical or different, represent, independently of each other, 0 or 1; n is equal to 1 or 2;
R, R' and R", which may be identical or different, are chosen, independently of each other, from a linear or branched alkyl radical containing from 1 to 12 carbon atoms, a linear or branched alkenyl radical containing from 2 to 12 carbon atoms, and an aryl radical containing from 6 to 10 carbon atoms; R, R' and R" possibly being substituted with radicals chosen from alkyl, alkenyl, aryl and halogen, and possibly containing one or more heteroatoms chosen from O, S, N, P and Si; R and R' also possibly forming, together with the atoms that bear them, a hydrocarbon-based cyclic structure optionally containing one or more heteroatoms chosen from O, S and N, said cyclic structure comprising in total 5, 6, 7, 8 or 9 ring members; and
b) from 10 ppm to 2%, by weight relative to the total weight of the composition, of at least one odor-masking agent comprising at least one compound chosen from monoesters, diesters andor triesters, alcohols, aldehydes, ketones, and terpenes, wherein the aldehydes and ketones are of formula R$^a$—CO—R$^b$, in which R$^a$ represents a linear or branched hydrocarbon-based chain comprising from 1 to 6 carbon atoms, optionally comprising one or more unsaturation(s) in the form of double bonds, and R$^b$ represents a hydrogen atom, a cyclic hydrocarbon-based chain or a linear or branched hydrocarbon-based chain optionally substituted with a cyclic structure, R$^b$ comprising from 6 to 12 carbon atoms, optionally comprising one or more unsaturation(s) in the form of double bonds and being optionally substituted with one or more hydroxyl groups.

2. The composition as claimed in claim 1, wherein the content of the odor-masking agent(s) b) is between 0.001% and 0.2% by weight relative to the total weight of the composition.

3. The composition as claimed in claim 1, wherein a represents 0, —(Y)$_b$—represents —(S)$_x$—, in which x represents 0 or 1, and R and R' are identical and chosen, independently of each other, from a linear or branched alkyl radical comprising from 1 to 12 carbon atoms, a linear or branched alkenyl radical comprising from 2 to 12 carbon atoms, and an aryl radical.

4. The composition as claimed in claim 1, wherein component a) of the composition according to the present invention:
corresponds to formula (1'):

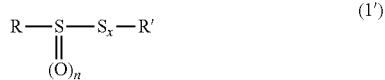

in which R is chosen from a linear or branched alkyl radical containing from 1 to 4 carbon atoms, a linear or branched alkenyl radical containing from 2 to 4 carbon atoms, and an aryl radical, n is equal to 1 or 2; x represents 0 or 1; Rs is chosen from a linear or branched alkyl radical containing from 1 to 4 carbon atoms, a linear or branched alkenylene radical containing from 2 to 4 carbon atoms, and an aryl radical;

corresponds to formula (1):

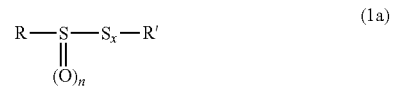

in which R and R', which may be identical or different, are chosen from a linear or branched alkyl radical containing from 1 to 4 carbon atoms, a linear or branched alkenyl radical containing from 1 to 4 carbon atoms, and a phenyl radical; n is equal to 1 or 2; and x is equal to 0; or
is DSMO.

5. The composition as claimed in claim 1, wherein the odor-masking agent b) comprises one or more compounds chosen from:
b1) monoesters;
b2) diesters and/or triesters;
b3) alcohols, comprising from 1 to 30 carbon atoms, said carbon atoms forming a linear or branched chain optionally comprising one or more unsaturation(s) in the form of double bonds, and optionally comprising a 5- or 6-membered cyclic structure, which is saturated or partially or totally unsaturated;
b4) aldehydes and ketones of formula R$^a$—CO—R$^b$, in which R$^a$ represents a linear or branched hydrocarbon-based chain comprising from 1 to 6 carbon atoms, optionally comprising one or more unsaturation(s) in the form of double bonds, and R$^b$ represents a hydrogen atom, a cyclic hydrocarbon-based chain or a linear or branched hydrocarbon-based chain optionally substituted with a cyclic structure, R$^b$ comprising from 6 to 12 carbon atoms, optionally comprising one or more unsaturation(s) in the form of double bonds and being optionally substituted with one or more hydroxyl groups; and
b5) terpenes.

6. The composition as claimed in claim 5, wherein b1) is chosen from esters of saturated or unsaturated C$_2$-C$_{20}$ acids, and also mixtures thereof.

7. The composition as claimed in claim 5, wherein b2) is chosen from ortho-phthalates, citrates, and malonates.

8. The composition as claimed in claim 5, wherein b3) is chosen from menthol, neomenthol, phenylethyl alcohol, benzyl alcohol, citronellol, dihydromyrcenol, dihydroterpineol, dimetol, ethyllinalool, geraniol, linalool, tetrahydrolinalool, tetrahydromyrcenol, nerol, and also mixtures of two or more thereof.

9. The composition as claimed in claim 5, wherein b4) is chosen from propionaldehyde, butyraldehyde, valeraldehyde, capraldehyde, benzaldehyde, geranial, neral, citronellal and, in general, aldehydes containing hydrocarbon-based groups comprising one or more unsaturations of olefinic type, menthone, isomenthone, 1,8-cineole, ascaridole, flavonone, damascones, damascenones, ionones, irisones, methylionones, frambinone, and also mixtures of two or more thereof in all proportions.

10. The composition as claimed in claim 5, wherein b5) is chosen from terpinenes, myrcene, limonene, terpinolene, pinenes, sabinene, camphene, mixtures of two or more thereof, and also terpene-based essences.

11. The composition as claimed in claim 5, wherein the odor-masking agent is chosen from odor-masking agents comprising:
at least one component b1);
at least one component b1) and at least one component b2);

at least one component b1) and at least one component b3);
at least one component b1) and at least one component b4);
at least one component b1) and at least one component b5);
at least one component b1), at least one component b2) and at least one component b3);
at least one component b1), at least one component b2) and at least one component b4);
at least one component b1), at least one component b2) and at least one component b5);
at least one component b1), at least one component b3) and at least one component b4);
at least one component b1), at least one component b3) and at least one component b5);
at least one component b1), at least one component b2), at least one component b3) and at least one component b4);
at least one component b1), at least one component b2), at least one component b3) and at least one component b5);
at least one component b1), at least one component b2), at least one component b3), at least one component b4) and at least one component b5);
at least one component b2);
at least one component b2) and at least one component b3);
at least one component b2) and at least one component b4);
at least one component b2) and at least one component b5);
at least one component b2), at least one component b3) and at least one component b4);
at least one component b2), at least one component b3) and at least one component b5);
at least one component b2), at least one component b4) and at least one component b5);
at least one component b2), at least one component b3), at least one component b4) and at least one component b5);
at least one component b3);
at least one component b3) and at least one component b4);
at least one component b3) and at least one component b5);
at least one component b3), at least one component b4) and at least one component b5);
at least one component b4);
at least one component b4) and at least one component b5); and
at least one component b5).

12. The composition as claimed in claim 5, wherein the odor-masking agent comprises from 1% to 40% by weight of at least one monoester b1) relative to the total weight of composition b).

13. The composition as claimed in claim 5, wherein the odor-masking agent comprises from 10% to 70% by weight of at least one diester and/or triester b2) relative to the total weight of composition b).

14. The composition as claimed in claim 5, wherein the odor-masking agent comprises from 1% to 30% by weight of at least one alcohol b3) relative to the total weight of composition b).

15. The composition as claimed in claim 5, wherein the odor-masking agent comprises from 0.5% to 20% by weight of at least one aldehyde and/or ketone b4) relative to the total weight of composition b).

16. The composition as claimed in claim 5, wherein the odor-masking agent comprises up to 20% by weight of at least one terpene indicated in b5) relative to the total weight of composition b).

17. The composition as claimed in claim 1, wherein the odor-masking agent comprises:
b1) from 1% to 40% by weight of at least one monoester;
b2) from 10% to 70% by weight of at least one diester and/or triester;
b3) from 1% to 30% of at least one alcohol;
b4) from 0.5% to 20% of at least one aldehyde and/or ketone of formula $R^a$—CO—$R^b$, in which $R^a$ represents a linear or branched hydrocarbon-based chain comprising from 1 to 6 carbon atoms, optionally comprising one or more unsaturation(s) in the form of double bonds, and le represents a cyclic hydrocarbon-based chain or a linear or branched hydrocarbon-based chain optionally substituted with a cyclic structure, le comprising from 6 to 12 carbon atoms, optionally comprising one or more unsaturation(s) in the form of double bonds and being optionally substituted with one or more hydroxyl groups; and
b5) optionally up to 20% of at least one terpene.

18. The composition as claimed in claim 17, wherein the odor-masking agent comprises:
from 5% to 30% by weight of at least one monoester b1), chosen from isoamyl acetate, ethyl 2-methylbutyrate, isoamyl butyrate, phenylethyl acetate, ethyl caproate, benzyl acetate and hexyl acetate, and mixtures thereof;
from 20% to 60% by weight of at least one diester and/or triester b2) chosen from ortho-phthalates; citrates; malonates, and mixtures thereof;
from 5% to 25% of at least one alcohol, as described previously in b3);
from 1% to 10% of at least one ketone, as described previously in b4); and
from 1% to 10% of at least one terpene referenced above in b5).

19. The composition as claimed in claim 1, comprising:
a) from 50% to 95% by weight of at least one oxide of an organic sulfide of general formula (1);
b) from 10 ppm to 2%, relative to the total weight of the composition, of at least one odor-masking agent b); and
c) from 5% to 50% by weight of at least one cosolvent.

20. The composition as claimed in claim 19, wherein the cosolvent is chosen from compounds that are at least partially or totally soluble in oxides of organic sulfides a).

21. The composition as claimed in claim 19, comprising:
a) about 80% by weight of DMSO;
b) from 10 ppm to 2%, relative to the total weight of the composition, of masking agent comprising:
from 5% to 30% by weight of at least one monoester b1), chosen from isoamyl acetate, ethyl 2-methylbutyrate, isoamyl butyrate, phenylethyl acetate, ethyl caproate, benzyl acetate and hexyl acetate, and mixtures thereof;
from 20% to 60% by weight of at least one diester and/or triester b2) chosen from ortho-phthalates; malonates, and mixtures thereof;
from 5% to 25% of at least one alcohol, as described previously in b3);
from 1% to 10% of at least one ketone, as described previously in b4); and
from 1% to 10% of at least one terpene referenced above in b5); and
c) about 20% by weight of glycerol.

22. The composition of claim 2, wherein the content of the odor-masking agent(s) b) is between 100 ppm and 1000 ppm.

23. The composition of claim 20, wherein the cosolvent is chosen from carbonates, esters, ketones, amines, amides, and alcohols.

24. The composition of claim 20, wherein the cosolvent is chosen from saturated alcohols comprising from 1 to 10 carbon atoms.

25. The composition of claim 20, wherein the cosolvent is chosen from methanol, ethanol, propanol, butanol, pentanol, ethylene glycol, propylene glycol, and glycerol (1,2,3-propanetriol).

26. The composition of claim 1, wherein the at least one oxide of an organic sulfide of general formula (1) is present in the composition in an amount of at least 70% by weight.

27. The composition of claim 1, wherein the at least one oxide of an organic sulfide of general formula (1) is present in the composition in an amount of at least 80% by weight.

28. The composition of claim 6, wherein b 1) is selected from the group consisting of acetates, propionates, butyrates, methylbutyrates, pentanoates, hexanoates, heptanoates, caproates, oleates, and linoleates or linolenates of ethyl, propyl, butyl, pentyl, 2-methylbutyl, isoamyl, hexyl, benzyl, phenylethyl, menthyl, and carvyl.

29. The composition of claim 5, wherein the alcohols are monoalcohols.

* * * * *